United States Patent [19]

Partridge et al.

[11] Patent Number: 4,820,402

[45] Date of Patent: Apr. 11, 1989

[54] HYDROCRACKING PROCESS WITH IMPROVED DISTILLATE SELECTIVITY WITH HIGH SILICA LARGE PORE ZEOLITES

[75] Inventors: Randall D. Partridge, Princeton; Rene B. LaPierre, Medford, both of N.J.

[73] Assignee: Mobil Oil Corporation, New York, N.Y.

[21] Appl. No.: 56,341

[22] Filed: May 27, 1987

Related U.S. Application Data

[60] Continuation of Ser. No. 744,897, Jun. 17, 1985, abandoned, which is a continuation of Ser. No. 586,483, Mar. 5, 1984, abandoned, which is a division of Ser. No. 379,400, May 18, 1982.

[51] Int. Cl.$^4$ .................. C10G 47/18; C10G 47/20
[52] U.S. Cl. ................................ 208/111; 502/79
[58] Field of Search ........................... 208/111, 120

[56] References Cited

U.S. PATENT DOCUMENTS

| | | | |
|---|---|---|---|
| Re. 28,341 | 2/1975 | Wadlinger et al. | 208/120 |
| 3,008,895 | 11/1961 | Hansford et al. | 208/68 |
| 3,130,006 | 4/1964 | Rabo et al. | 23/110 |
| 3,132,089 | 5/1964 | Hass et al. | 208/89 |
| 3,132,090 | 5/1964 | Helfrey et al. | 208/89 |
| 3,159,568 | 12/1964 | Price | 208/89 |
| 3,236,761 | 2/1966 | Rabo et al. | 208/111 |
| 3,236,762 | 2/1966 | Rabo et al. | 208/111 |
| 3,267,022 | 8/1966 | Hansford | 208/111 |
| 3,269,934 | 8/1966 | Hansford | 208/111 |
| 3,287,252 | 11/1966 | Young | 208/59 |
| 3,293,192 | 12/1966 | Maher et al. | 252/430 |
| 3,308,069 | 3/1967 | Wadlinger et al. | 252/455 |
| 3,354,077 | 11/1967 | Hansford | 208/111 |
| 3,392,108 | 7/1968 | Mason et al. | 208/111 |
| 3,449,070 | 6/1969 | McDaniel et al. | 23/111 |
| 3,472,758 | 10/1969 | Stine et al. | 208/59 |
| 3,523,887 | 8/1970 | Hanson et al. | 208/111 |
| 3,524,809 | 8/1970 | Hansford | 208/111 |
| 3,549,518 | 12/1970 | Mason | 208/111 |
| 3,553,103 | 1/1971 | Burbidge et al. | 208/111 |
| 3,554,899 | 1/1971 | Hansford | 208/111 |
| 3,617,483 | 11/1971 | Child et al. | 208/59 |
| 3,644,197 | 2/1972 | Kelley et al. | 208/89 |
| 3,644,200 | 2/1972 | Young | 208/120 |
| 3,655,551 | 4/1972 | Hass et al. | 208/59 |
| 3,663,430 | 5/1972 | Morris | 208/111 |
| 3,728,251 | 4/1973 | Kelley et al. | 208/89 |
| 3,761,396 | 9/1973 | Pickert et al. | 208/111 |
| 3,781,199 | 12/1973 | Ward | 208/89 |
| 3,836,454 | 9/1974 | Hansford | 208/111 |
| 3,847,792 | 11/1974 | Berger | 208/60 |
| 3,867,277 | 5/1975 | Ward | 208/111 |
| 3,894,930 | 7/1975 | Hensley, Jr. | 208/60 |
| 3,894,939 | 7/1975 | Garwood et al. | 208/111 |
| 3,897,327 | 7/1975 | Ward | 208/111 |
| 3,923,640 | 12/1975 | Wight | 208/111 |
| 3,923,641 | 12/1975 | Morrison | 208/111 |
| 3,926,782 | 12/1975 | Plank et al. | 208/135 |
| 3,929,672 | 12/1975 | Ward | 252/455 Z |
| 3,937,791 | 2/1976 | Garwood et al. | 423/328 |
| 4,040,944 | 8/1977 | Kelley et al. | 208/89 |
| 4,054,539 | 10/1977 | Henslay, Jr. | 208/111 |
| 4,093,560 | 7/1978 | Kerr et al. | 252/455 |
| 4,097,365 | 6/1978 | Ward | 208/111 |
| 4,104,320 | 8/1978 | Bernard et al. | 208/138 |

(List continued on next page.)

FOREIGN PATENT DOCUMENTS

| | | |
|---|---|---|
| 1149307 | 7/1983 | Canada .......................... 208/111 |
| 0014291 | 8/1980 | European Pat. Off. . |
| 0023802 | 2/1981 | European Pat. Off. . |
| 0028938 | 5/1981 | European Pat. Off. . |
| 2836076 | 3/1979 | Fed. Rep. of Germany . |
| 2572307 | 5/1986 | France ............................ 502/64 |

OTHER PUBLICATIONS

Charles L. Thomas, Catalytic Processes and Proven Catalysts, New York and London, Academic Press, 1970; pp. 25-27, 173.

*Primary Examiner*—Olik Chaudhuri
*Attorney, Agent, or Firm*—Alexander J. McKillop; Charles J. Speciale; Marina V. Schneller

[57] ABSTRACT

A hydrocracking process in which improved selectivity for the production of distillate range (165° C.–343° C.) products is obtained by the use of a catalyst containing a highly siliceous large pore zeolite as the acidic component. Suitable zeolites include zeolites, Y, ZSM-20 and beta with structural silica:alumina ratios of at least 50:1.

22 Claims, 1 Drawing Sheet

U.S. PATENT DOCUMENTS

| | | | |
|---|---|---|---|
| 4,191,638 | 3/1980 | Plank et al. | 208/139 |
| 4,257,872 | 3/1981 | LaPierre et al. | 208/59 |
| 4,276,151 | 6/1981 | Plank et al. | 208/138 |
| 4,305,808 | 12/1981 | Bowes et al. | 208/111 |
| 4,326,947 | 4/1982 | Sawyer | 208/111 |
| 4,401,556 | 8/1983 | Bezman et al. | 208/111 |
| 4,411,770 | 10/1983 | Chen et al. | 208/111 |
| 4,419,220 | 12/1983 | LaPierre et al. | 208/111 |
| 4,419,271 | 12/1983 | Ward | 502/65 |
| 4,431,516 | 2/1984 | Baird et al. | 208/111 |
| 4,431,527 | 2/1984 | Miller et al. | 208/254 |
| 4,456,527 | 6/1984 | Buss et al. | 208/89 |
| 4,456,693 | 6/1984 | Welsh | 502/65 |
| 4,481,104 | 11/1984 | Walsh | 208/120 |
| 4,486,296 | 12/1984 | Oleck et al. | 208/111 |
| 4,500,645 | 2/1985 | Fuchikami et al. | 502/65 |
| 4,517,073 | 5/1985 | Ward et al. | 208/111 |
| 4,517,074 | 5/1985 | Ward | 208/111 |
| 4,563,434 | 1/1986 | Ward | 502/66 |
| 4,565,621 | 1/1986 | Ward | 208/111 |
| 4,575,416 | 3/1986 | Chester et al. | 208/111 |
| 4,576,711 | 3/1986 | Ward et al. | 208/111 |
| 4,584,287 | 4/1986 | Ward | 502/65 |
| 4,600,498 | 7/1986 | Ward | 208/111 |
| 4,610,973 | 9/1986 | Ward | 502/65 |

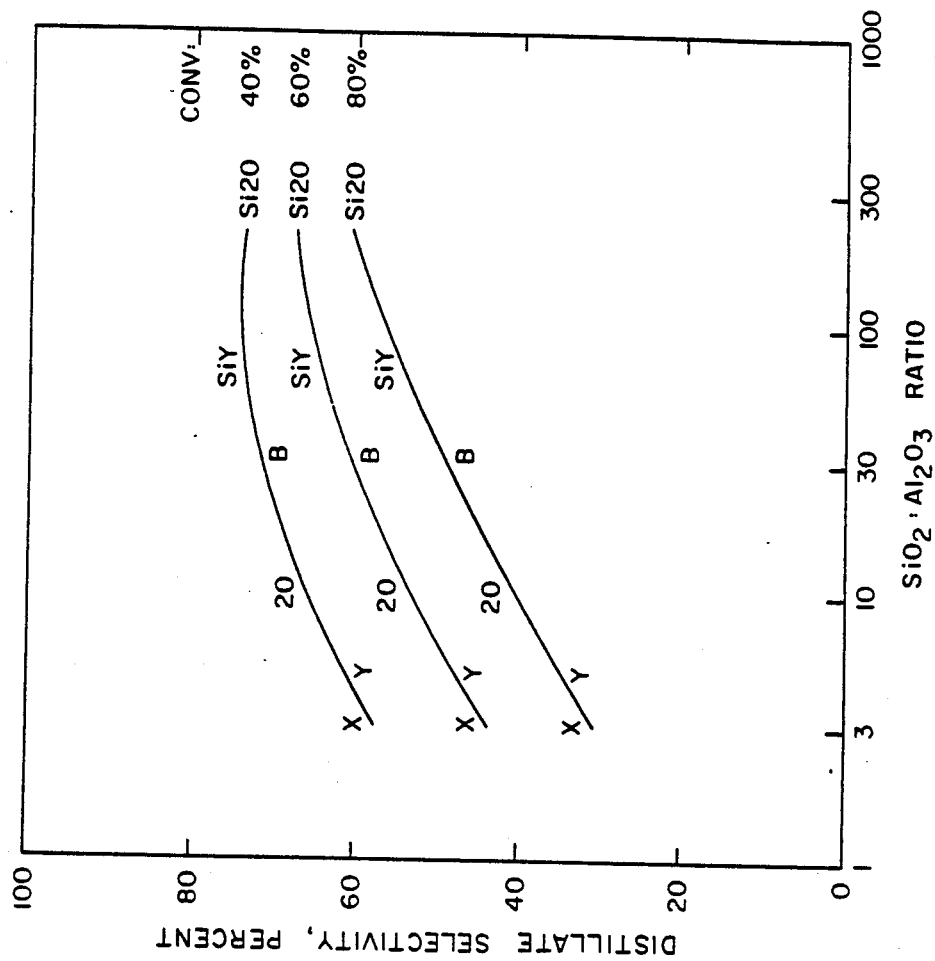

ately low
HYDROCRACKING PROCESS WITH IMPROVED DISTILLATE SELECTIVITY WITH HIGH SILICA LARGE PORE ZEOLITES This is a continuation of copending application Ser. No. 744,897, filed on June 17, 1985, which is a continuation of copending application Ser. No. 586,483, filed on Mar. 5, 1984, both now abandoned, which is a division of copending application Ser. No. 379,400, filed on May 18, 1982.

FIELD OF THIS INVENTION

This invention relates to a hydrocracking process with improved selectivity towards the production of distillate range materials.

REFERENCE TO RELATED APPLICATIONS

U.S. patent application Ser. No. 379,421, filed May 18, 1982 concurrently with this application, by R. B. LaPierre and R. D. Partridge, entitled "Simultaneous Catalytic Hydrocracking and Hydrodewaxing" of Hydrocarbon Oils with Zeolite Beta describes and claims a process for simultaneous hydrocracking and dewaxing using zeolite beta.

THE PRIOR ART

Hydrocracking is a versatile petroleum refining process which enjoys widespread use in the refining industry. Hydrocracking has the ability to process a wide range of difficult feedstocks into a variety of desirable products. Feedstocks which may be treated by this process include heavy naphthas, kerosenes, refractory catalytically cracked cycle stocks and high boiling virgin and coker gas oils. At high severities, hydrocracking can convert these materials to gasoline and lower boiling paraffins; lesser severities permit the higher boiling feedstocks to be converted into lighter distillates such as diesel fuels and aviation kerosenes.

Hydrocracking is conventionally carried out at moderate temperatures of 350° C. to 450° C. (650° F. to 850° F.) and at high pressures, over 7,000 kPa (1,000 psig) because the thermodynamics of the hydrocracking process become unfavorable at higher temperatures. In addition, high hydrogen pressures, usually at least 20,000 kPa are usually required to prevent catalyst aging and so to maintain sufficient activity to enable the process to be operated with a fixed bed of catalyst for periods of one to two years without the need for regeneration. The catalysts used for hydrocracking usually comprise a transition metal such as nickel, cobalt, tungsten or molybdenum on an acidic support such as alumina or silica-alumina although noble metals such as platinum may also be used. Combinations of metals such as cobalt with molybdenum have been found to be extremely effective with a wide variety of feedstocks as has the presulfiding technique which is now widely employed.

During the hydrocracking reaction the bulky polycyclic compounds in the feedstock enter the pore structure of the catalyst where they are cracked and hydrogenated to form lower molecular weight monocyclic aromatics with saturated side chains. Because these reactions generally predominate in the hydrocracking process as a whole, it has generally been considered necessary that the acidic component should permit ready access to the bulky polycyclic aromatics and for this reason, porous supports of large pore size have usually been selected. Amorphous silica-alumina supports have frequently been used in commercial processes because they have a suitably large pore size, as have large pore crystalline aluminosilicate zeolites of the faujasite family, faujasite, zeolite X and zeolite Y. In some processes which have been proposed, the amorphous material is used together with a crystalline zeolite, as described in U.S. Pat. No. 3,523,887.

Hydrocracking processes using hydrogen form zeolite Y as the acidic component are described, for example, in U.S. Pat. Nos. 3,269,934 and 3,524,809. Zeolite ZSM-20 which resembles faujasite in certain aspects of structure, but which has a higher silica:alumina ratio usually within the range from 7:1 to 10:1, has also been proposed for use as the acidic component of a hydrocracking catalyst in U.S. Pat. No. 4,021,331 and European Pat. No. 14,291. The silica:alumina ratios of these catalysts has remained, however, at a relatively low value, not higher than about 7:1 or 8:1.

SUMMARY OF THE INVENTION

It has now been found that the selectivity of the catalysts for the production of distillate range materials is enhanced by the use of catalysts which have higher silica:alumina ratios than those used in the past. It is believed that the higher silica:alumina ratios of the present catalysts result in a decrease in the density of the acidic sites in the catalyst and that this, in turn, reduces the severity of cracking which takes place. In this way, the heavy oils in the feedstock are converted preferentially to the higher boiling distillate range products rather than to the more volatile materials in the gasoline boiling range. The hydrocracked product is very low in fractions boiling below 150° C. (about 300° F.) and in most cases the product will have a boiling range of 150° to 340° C. (about 300° to 650° F.).

The catalysts used in the present process are large pore crystalline zeolites with silica:alumina ratios of 10:1 or higher. Ratios much higher than this e.g. 50:1, 100:1 or 200:1 have been found to give very good distillate selectivities. The zeolite is used in combination with a hydrogenation-dehydrogenation component such as a metal of Groups VA, VIA or VIIIA of the Periodic Table (the Periodic Table used in this specification is the table approved by IUPAC and the U.S. National Bureau of Standards, as shown for instance in the table of the Fisher Scientific Company, Catalog No. 5-702-10).

In addition to the improved selectivity for the production of distillate range products the present process is also capable of decreasing the hydrogen consumption, particularly at higher silica:alumina ratios in the zeolite catalyst. The production of gas and naphtha also decreases at higher silica:alumina ratios.

BRIEF DESCRIPTION OF THE DRAWINGS

The single FIGURE of the accompanying drawings is a graph which shows the improvement in distillate selectivity wrought by the use of the high silica zeolite catalysts.

DESCRIPTION OF PREFERRED EMBODIMENTS

Feedstock

The present process may be used for hydrocracking a variety of feedstocks such as crude petroleum, reduced crudes, vacuum tower residua, coker gas oils, cycle oils, FCC tower bottoms, vacuum gas oils, deasphalted residua and other heavy oils. The feedstock will contain a substantial amount boiling above 260° C. (500° F.) and will normally have an initial boiling point of about 290° C. (about 550° F.), more usually about 340° C. (650° F.). Typical boiling ranges will be about 340° C. to 565° C. (650° F. to 1050° F.) or about 340° C. to 510° C. (650° F. to 950° F.) but oils with a narrower boiling range may, of course, also be processed, for example, those with a boiling range of about 340° C. to 455° C. (650° F. to 850° F.). Heavy gas oils are often of this kind as are cycle oils and other non-residual materials. Oils desired from coal, shale or tar sands may also be treated in this way. It is possible to co-process materials boiling below 260° C. (500° F.) but they will be substantially unconverted. Feedstocks containing lighter ends of this kind will normally have an initial boiling point above 150° C. (about 300° F.). Feedstock components boiling in the range 290° to 340° C. (about 550° to 650° F.) can be converted to products boiling from 230° to 290° C. (about 450° to 550° F.) but the heavier ends of the feedstock are converted preferentially to the more volatile components and therefore the lighter ends may remain unconverted unless the process severity is increased sufficiently to convert the entire range of components.

Catalyst

The catalyst used in the present process comprises a large pore crystalline zeolite as the acidic component and a hydrogenation-dehydrogenation component which may be a noble metal or metals or a non-noble metal or metals. Suitable noble metals include platinum, palladium, and other members of the platinum group such as iridium and rhodium. Suitable non-noble metals include those of Groups VA, VIA and VIIIA of the Periodic Table. Preferred non-noble metals are chromium, molybdenum, tungsten, cobalt and nickel and combinations of these metals such as cobalt-molybdenum, cobalt-nickel, nickel-tungsten and cobalt-nickel-tungsten. Non-noble metal components may be pre-sulfided prior to use by exposure to a sulfur-containing gas such as hydrogen sulfide at an elevated temperature to convert the oxide form to the corresponding sulfide form of the metal.

The metal may be incorporated into the catalyst by any suitable method such as impregnation or exchange onto the zeolite. The metal may be incorporated in the form of a cationic, anionic or neutral complex such as $Pt(NH_3)_4^{2+}$ and cationic complexes of this type will be found convenient for exchanging metals onto the zeolite. Anionic complexes such as the vanadate or metatungstate ions are useful for impregnating metals into the catalysts.

The amount of the hydrogenation-dehydrogenation component is suitably from 0.01 to 10 percent by weight, normally 0.1 to 5 percent by weight, although this will, of course, vary with the nature of the component, less of the highly active noble metals, particularly platinum, being required than of the less active base metals.

The acidic component of the hydrocracking catalyst is a large pore crystalline zeolite. Many crystalline alumino-silicate zeolites are known. Some occur (at least so far) only in nature, for instance paulingite and merlinoite: some occur only as a result of synthesis, for instance zeolites A and ZSM-5: and some occur in both natural and synthetic forms for instance mordenite, a synthetic counterpart of which is known as Zeolon, and faujasite, synthetic counterparts of which are known as zeolites X and Y. Counterparts are of course demonstrated as such by correspondence of their X-ray diffraction data, the indicia by means of which the individuality of a zeolite is established. Such data are a manifestation of the particular geometry of the three-dimensional lattice, formed of $SiO_4$ an $AlO_4$ tetrahedra cross-linked by the sharing of oxygen atoms and including sufficient cationic complement to balance the resulting negative charge on the $AlO_4$ tetrahedra, of which a zeolite consists.

The chemical formula of a zeolite is thus

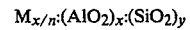

$$M_{x/n}:(AlO_2)_x:(SiO_2)_y$$

where M is a cation of valence n and x and y are the number of aluminum and silicon atoms, respectively, in the unit cell. This expression is however frequently transformed into the mole ratio of oxides form,

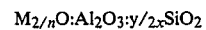

$$M_{2/n}O:Al_2O_3:y/2xSiO_2$$

which is of course empirically ascertainable and thus the only formula which can be ascribed to a zeolite when its unit cell contents are unknown. Since the only significant quantity in such a formula is the term y/2x, and since this term (which is almost invariably a range) can usually be satisfied by many zeolites of widely differing lattice geometry, chemical formula is not of value in establishing the identity of a zeolite. Furthermore, such a formula frequently expresses artefact when empirically derived, the cationic-valence-/aluminum-atoms ratio deviating from the unity which it must in fact be; and it fails to provide for zeolites whose lattice structure can be brought into existence from reaction mixtures from which alumina is excluded.

The zeolites used in the present catalysts have a porous crystalline structure with pores which have at least one dimension in excess of 6 Angstroms. The zeolite is also to have a silica:alumina ratio of at least 10:1 and a hydrocarbon sorption capacity for n-hexane of at least 6 percent. The hydrocarbon sorption capacity is determined by measuring the sorption at 25° C., 20 mm Hg (2666 Pa) hydrocarbon pressure in an inert carrier such as helium.

Hydrocarbon sorption capacity (%) =

$$\frac{\text{Wt. of hydrocarbon sorbed}}{\text{Wt. of zeolite}} \times 100$$

The sorption test is conveniently carried out in a TGA with helium as a carrier gas flowing over the zeolite at 25° C. The hydrocarbon of interest e.g. n-hexane is introduced into the gas stream adjusted to 20 mm Hg hydrocarbon pressure and the hydrocarbon uptake, measured as the increase in zeolite weight is recorded. The sorption capacity may then be calculated as a percentage.

Consistent with the prescribed values of pore size and hydrocarbon sorption the zeolite should also have a Constraint Index of up to 2.0, usually 0.5 to 2.0. Constraint Index provides a convenient measure of the extent to which a zeolite provides controlled access, for molecules of varying sizes to its internal structure: zeolites which provide highly restricted access to and egress from the internal structure have a high value for the Constraint Index and zeolites of this kind usually have pores of small size. Contrariwise, zeolites which provide relatively free access to the internal zeolite structure have a low value for the Constraint Index. The method by which Constraint Index is determined is described fully in U.S. Pat. No. 4,016,218 to which reference is made for details of the method together with examples of Constraint Index for some typical zeolites. Because Constraint Index is related to the crystalline structure of the zeolite but is nevertheless determined by means of a test which exploits the capacity of the zeolite to engage in a cracking reaction, that is, a reaction dependent upon the possession of acidic sites and functionality in the zeolite, the sample of zeolite used in the test should be representative of zeolitic structure whose Constraint Index is to be determined and should also possess requisite acidic functionality for the test. Acidic functionality may, of course, be varied by artifices including base exchange, steaming or control of silica:alumina ratio.

Zeolites of the requisite pore size, hydrocarbon sorption and Constraint Index include certain faujasites, especially zeolite Y and zeolite ZSM-20 together with zeolites beta, ZSM-4, ZSM-12, ZSM-38 and ZSM-50. Of these, zeolites Y, beta and ZSM-20 are particularly useful in the present process because they may be conveniently prepared in forms which possess the desired highly siliceous nature.

Zeolite ZSM-4 is described in U.S. Pat. No. 3,923,639; zeolite ZSM-12 is described in U.S. Pat. No. 3,832,449; zeolite ZSM-38 is described in U.S. Pat. No. 4,046,859, zeolite ZSM-50 is described in U.S. patent application Ser. No. 343,531 of E. W. Valyocsik, filed Jan. 28, 1982 and entitled "Zeolite ZSM-50, Method of Preparing Same and Catalytic Conversion Therewith". Highly siliceous forms of zeolites ZSM-5, and ZSM-12 are described in U.S. Pat. No. Re. 29,948 and Applications Ser. Nos. 003,144 and 003,146, both filed Jan. 15, 1979. Reference is made to these patents and applications for details of these zeolites and their preparation.

The Constraint Indices of certain of these zeolites are given below for reference:

| Zeolite | Constraint Index |
| --- | --- |
| REY | 0.4 |
| ZSM-4 | 0.5 |
| Beta | 0.6 |
| ZSM-12 | 2 |
| ZSM-38 | 2 |

If the zeolite selected may be produced in the desired highly siliceous form by direct synthesis, this will often be the most convenient method for obtaining it. Zeolite beta, for example, is known to be capable of being synthesized directly in forms having silica:alumina ratios up to 100:1, as described in U.S. Pat. No. 3,308,069 and U.S. Pat. No. Re. 28,341 which describe zeolite beta, its preparation and properties in detail and reference is made to these patents for these details. Zeolite Y, on the other hand, can be synthesized only in forms which have silica:alumina ratios up to about 5:1 and in order to achieve higher ratios, resort may be made to various techniques to remove structural aluminum so as to obtain a more highly siliceous zeolite. Zeolite ZSM-20 may be directly synthesized with silica:alumina ratios of 7:1 or higher, typically in the range of 7:1 to 10:1, as described in U.S. Pat. Nos. 3,972,983 and 4,021,331 to which reference is made for details of this zeolite, its preparation and properties. Zeolite ZSM-20 also may be treated by various methods to increase its silica:alumina ratio.

Control of the silica:alumina ratio of the zeolite in its as-synthesized form may be exercised by an appropriate selection of the relative proportions of the starting materials, especially the silica and alumina precursors, a relatively smaller quantity of the alumina precursor resulting in a higher silica:alumina ratio in the product zeolite, up to the limit of the synthetic procedure. If higher ratios are desired and alternative synthesis affording the desired high silica:alumina ratios are not available, other techniques such as those described below may be used in order to prepare the desired highly siliceous zeolites.

It should be understood that the silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as the dealuminization methods described below which result in the presence of ionic aluminum free of the zeolite structure are employed. Due care should therefore be taken to ensure that the framework silica:alumina ratio is correctly determined.

A number of different methods are known for increasing the structural silica:alumina ratio of various zeolites. Many of these methods rely upon the removal of aluminum from the structural framework of the zeolite by chemical agents appropriate to this end. A considerable amount of work on the preparation of aluminum deficient faujasites has been performed and is reviewed in Advances in Chemistry Series No. 121, Molecular Sieves, G. T. Kerr, American Chemical Society, 1973. Specific methods for preparing dealuminized zeolites are described in the following, and reference is made to them for details of the method: Catalysis by Zeolites (International Symposium on Zeolites, Lyon, Sept. 9-11, 1980), Elsevier Scientific Publishing Co., Amsterdam, 1980 (dealuminization of zeolite Y with silicon tetrachloride); U.S. Pat. No. 3,442,795 and G.B. No. 1,058,188 (hydrolysis and removal of aluminum by chelation); G.B. No. 1,061,847 (acid extraction of aluminum); U.S. Pat. No. 3,493,519 (aluminum removal by steaming and chelation); U.S. Pat. No. 3,591,488 (aluminum removal by steaming); U.S. Pat. No. 4,273,753 (dealuminization by silicon halide and oxyhalides); U.S. Pat. No. 3,691,099 (aluminum extraction with acid); U.S. Pat. No. 4,093,560 (dealuminization by treatment with salts); U.S. Pat. No. 3,937,791 (aluminum removal with Cr(III) solutions); U.S. Pat. No. 3,506,400 (steaming followed by chelation); U.S. Pat. No. 3,640,681 (extraction of aluminum with acetylacetonate followed by dehydroxylation); U.S. Pat. No. 3,836,561 (removal of aluminum with acid); DE-OS No. 2,510,740 (treatment of zeolite with chlorine or chlorine-contrary gases at high temperatures), NL No. 7,604,264 (acid extraction), JA No. 53,101,003 (treatment with EDTA or other materials to remove aluminum) and J. Catalysis 54 295 (1978) (hydrothermal treatment followed by acid extraction).

Because of their convenience and practicality the preferred dealuminization methods for preparing the present highly siliceous zeolites are those which rely upon acid extraction of the aluminum from the zeolite. It has been found that zeolite beta may be readily dealuminized by acid extraction and details of a suitable method are given in U.S. patent application Ser. No. 379,399 filed May 18, 1982 now abandoned, by R. B. LaPierre and S. S. Wong, entitled "High Silica Zeolite Beta", and reference is made to this application for details of the method.

Briefly, the method comprises contacting the zeolite with an acid, preferably a mineral acid such as hydrochloric acid. The dealuminization proceeds readily at ambient and mildly elevated temperatures and occurs with minimal losses in crystallinity, to form high silica forms of zeolite beta with silica:alumina ratios of at least 100:1, with ratios of 200:1 or even higher being readily attainable.

The zeolite is conveniently used in the hydrogen form for the dealuminization process although other cationic forms may also be employed, for example, the sodium form. If these other forms are used, sufficient acid should be employed to allow for the replacement by protons of the original cations in the zeolite. The zeolite should be used in a convenient particle size for mixing with the acid to form a slurry of the two components. The amount of zeolite in the slurry should generally be from 5 to 60 percent by weight.

The acid may be a mineral acid i.e., an inorganic acid or an organic acid. Typical inorganic acids which can be employed include mineral acids such as hydrochloric, sulfuric, nitric and phosphoric acids, peroxydisulfonic acid, dithionic acid, sulfamic acid, peroxymonosulfuric acid, amidosulfonic acid, nitrosulfonic acid, chlorosulfuric acid, pyrosulfuric acid, and nitrous acid. Representative organic acids which may be used include formic acid, trichloroacetic acid, and trifluoroacetic acid.

The concentration of added acid should be such as not to lower the pH of the reaction mixture at an undesirably low level which could affect the crystallinity of the zeolite undergoing treatment. The acidity which the zeolite can tolerate will depend, at least in part, upon the silica:alumina ratio of the starting material. Generally, it has been found that zeolite beta can withstand concentrated acid without undue loss in crystallinity but as a general guide, the acid will be from 0.1N to 4.0N, usually 1 to 2N. These values hold good regardless of the silica:alumina ratio fo the zeolite beta starting material. Stronger acids tend to effect a relatively greater degree of aluminum removal than weaker acids.

Higher silica:alumina ratios in the product may be obtained with starting materials of relatively lower silica:alumina ratio e.g., below 30:1. Silica:alumina ratios for the starting material below 40:1, especially below 30:1, may therefore be preferred in order to achieve the greater degree of dealuminization.

The dealuminization reaction proceeds readily at ambient temperatures but mildly elevated temperatures may be employed e.g. up to 100° C. The duration of the extraction will affect the silica:alumina ratio of the product since extraction, being diffusion controlled, is time dependent. However, because the zeolite becomes progressively more resistant to loss of crystallinity as the silica:alumina ratio increases i.e. it becomes more stable as the aluminum is removed, higher temperatures and more concentrated acids may be used towards the end of the treatment than at the beginning without the attendant risk of losing crystallinity.

After the extraction treatment, the product is water washed free of impurities, preferably with distilled water, until the effluent wash water has a pH within the approximate range of 5 to 8.

Catalytic materials for particular uses can be prepared by replacing the cations as required with other metallic or ammoniacal ions. If calcination is carried out prior to ion exchange, some or all of the resulting hydrogen ions can be replaced by metal ions in the ion exchange process. The silica:alumina ratio will be at least 100:1 and preferably at least 150:1. Ratios of 200:1 or higher e.g. 250:1, 300:1, 400:1 or 500:1 may be obtained by use of this procedure. If desired, the zeolite may be steamed prior to acid extraction so as to increase the silica:alumina ratio and render the zeolite more stable to the acid. The steaming may also serve to increase the ease with which the aluminum is removed and to promote the retention of crystallinity during the extraction procedure.

Highly siliceous forms of zeolite Y may be prepared by steaming or by acid extraction of structural aluminum (or both) but because zeolite Y in its normal, as-synthesized condition, is unstable to acid, it must first be converted to an acid-stable form. Methods for doing this are known and one of the most common forms of acid-resistant zeolite Y is known as "Ultrastable Y" (USY); it is described in U.S. Pat. Nos. 3,293,192 and 3,402,996 and the publication, Society of Chemical Engineering (London) Monograph Molecular Sieves, page 186 (1968) by C. V. McDaniel and P. K. Maher, and reference is made to these for details of the zeolite and its preparation. In general, "ultrastable" refers to Y-type zeolite which is highly resistant to degradation of crystallinity by high temperature and steam treatment and is characterized by a $R_2O$ content (wherein R is Na, K or any other akali metal ion) of less than 4 weight percent, preferably less than 1 weight percent, and a unit cell size less than 24.5 Angstroms and a silica to alumina mole ratio in the range of 3.5 to 7 or higher. The ultrastable form of Y-type zeolite is obtained primarily by a substantial reduction of the alkali metal ions an the unit cell size reduction of the alkali metal ions and the unit cell size reduction. The ultrastable zeolite is identified both by the smaller unit cell and the low alkali metal content in the crystal structure.

The ultrastable form of the Y-type zeolite can be prepared by successively base exchanging a Y-type zeolite with an aqueous solution of an ammonium salt, such as ammonium nitrate, until the alkali metal content of the Y-type zeolite is reduced to less than 4 weight percent. The base exchanged zeolite is then calcined at a temperature of 540° C. to 800° C. for up to several hours, cooled and successively base exchanged with an aqueous solution of an ammonium salt until the alkali metal content is reduced to less than 1 weight percent, followed by washing and calcination again at a temperature of 540° C. to 800° C. to produce an ultrastable zeolite Y. The sequence of ion exchange and heat treatment results in the substantial reduction of the alkali metal content of the original zeolite and results in a unit cell shrinkage which is believed to lead to the ultra high stability of the resulting Y-type zeolite.

The ultrastable zeolite Y may then be extracted with acid to produce a highly siliceous form of the zeolite. The acid extraction may be made in the same way as described above for zeolite beta.

Other methods for increasing the silica:alumina ratio of zeolite Y by acid extraction are described in U.S. Pat. Nos. 4,218,307, 3,591,488 and 3,691,099, to which reference is made for details of these methods.

A preferred method of preparing highly siliceous forms of zeolite Y and ZSM-20 by acid extraction of the stabilized zeolite is described in U.S. patent application Ser. No. 379,424, filed May 8, 1982 now abandoned, by R. B. LaPierre, R. D. Partridge and P. T. Reischmann and entitled "Method for Preparing Acid Stable Zeolites and High Silica Zeolites Prepared By It", and reference is made to that application for details of the method.

Zeolite ZSM-20 may be converted to more highly siliceous forms by a process similar to that used for zeolite Y: first, the zeolite is converted to an "ultrastable" form which is then dealuminized by acid extraction. The conversion to the ultrastable form may suitably be carried out by the same sequence of steps used for preparing ultrastable Y. The zeolite is successively base-exchanged to the ammonium form and calcined, normally at temperatures above 700° C. The calcination should be carried out in a deep bed in order to impede removal of gaseous products, as recommended in Advances in Chemistry Series, No. 121, op cit. Acid extraction of the "ultrastable" ZSM-20 may be effected in the same way as described above for zeolite beta.

It may be desirable to incorporate the catalyst in another material resistant to the temperature and other conditions employed in the process. Such matrix materials include synthetic or natural substances as well as inorganic materials such as clay, silica and/or metal oxides. The latter may be either naturally occurring or in the form of gelatinous precipitates or gels including mixtures of silica and metal oxides. Naturally occurring clays which can be composited with the catalyst include those of the montmorillonite and kaolin families. These clays can be used in the raw state as originally mined or initially subjected to calcination, acid treatment or chemical modification.

The catalyst may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia, and silica-magnesia zirconia. The matrix may be in the form of a cogel with the zeolite. The relative proportions of zeolite component and inorganic oxide gel matrix may vary widely with the zeolite content ranging from between 1 to 99, more usually 5 to 80, percent by weight of the composite. The matrix may itself possess catalytic properties generally of an acidic nature.

Process Conditions

The feedstock is contacted with the catalyst in the precence of hydrogen under hydrocracking conditions of elevated temperature and pressure. Conditions of temperature, pressure, space velocity and hydrogen ratio which are similar to those used in conventional hydrocracking may conveniently be employed. Process temperatures of 230° C. to 500° C. (450° F. to 930° F.) may conveniently be used although temperatures above 425° C. (800° F.) will normally not be employed as the thermodynamics of the hydrocracking reactions become unfavorable at temperatures above this point. Generally, temperatures of 300° C. to 425° C. (570° F. to 800° F.) will be employed. Total pressure is usually in the range of 500 to 20,000 kPa (58 to 2,886 psig) and the higher pressures within this range over 7,000 kPa (986 psig) will normally be preferred. The process is operated in the presence of hydrogen and hydrogen partial pressures will normally be from 600 to 6,000 kPa (72 to 2,305 psig). The ratio of hydrogen to the hydrocarbon feedstock (hydrogen circulation rate) will normally be from 10 to 3,500 n.l.l$^{-1}$ (56 to 19,660 SCF/bbl). The space velocity of the feedstock will normally be from 0.1 to 20 LHSV, preferably 0.1 to 1.0 LHSV.

The conversion may be conducted by contacting the feedstock with a fixed stationary bed of catalyst, a fixed fluidized bed or with a transport bed. A simple configuration is a trickle-bed operation in which the feed is allowed to trickle through a stationary fixed bed. With such a configuration, it is desirable to initiate the reaction with fresh catalyst at a moderate temperature which is of course raised as the catalyst ages, in order to maintain catalytic activity.

A preliminary hydrotreating step to remove nitrogen and sulfur and to saturate aromatics to naphthenes without substantial boiling range conversion will usually improve catalyst performance and permit lower temperatures, higher space velocities, lower pressures or combinations of these conditions to be employed.

The invention is illustrated in the following Examples in which all percentages and proportions are by weight unless the contrary is stated.

Examples 1 to 8 below illustrate the preparation of highly siliceous zeolite beta. Example 9 illustrates the preparation of highly siliceous zeolite ZSM-20. Example 10 illustrates the preparation of highly siliceous zeolite Y.

EXAMPLES 1-5

Samples of zeolite beta in the hydrogen form and having a silica:alumina ratio of 30:1 and a crystallinity of 100 percent were treated with excess hydrochloric acid of ranging normality at 25° C. or 95° C. under reflux for ranging periods as shown in Table 2 below. The silica:alumina ratios of the products were determined by ammonia desorption thermogravimetric analysis (TGA) and the crystallinities by X-ray peak area determination. The results are shown in Table 1 below.

TABLE 1

| | Dealuminization of Zeolite Beta | | |
|---|---|---|---|
| Ex | Treatment | Framework $SiO_2/Al_2O_3$ | Crystallinity (%) |
| 1 | 0.1 N HCl, 25°, 1 hr. | 40 | 100 |
| 2 | 0.1 N HCl, 95°, 1 hr. | 40 | 100 |
| 3 | 1 N HCl, 95°, 1 hr. | 190 | 85 |
| 4 | 2 N HCl, 95°, 1 hr. | 280 | 75 |
| 5 | 2 N HCl, 95°, 2 hr. | 400 | — |

Comparison of Examples 1 and 2 shows that the dealumination proceeds readily both at ambient and mildly elevated temperatures, although the degree of dealuminization effected is quite small with acid of this concentration. Use of more concentrated acid, as in Examples 3 and 4, gives a far greater degree of dealuminization a slight loss of crystallinity occurs but the product remains essentially a crystalline zeolite. Prolonged treatment, as shown in Example 5 produces a further increase in silica:alumina ratio with a relatively smaller loss in crystallinity, indicating the greater stability of the zeolite to acid attack at higher silica:alumina ratios.

EXAMPLES 6-8

Samples of zeolite beta having silica:alumina ratios (bulk assay) of 21.3:1, 23:1 and 35:1 were calcined in flowing nitrogen, increasing the temperature from room temperature to 500° C. at 1°/minute, and then holding at 500° C. for 4 hours. At 500° C. the zeolites were air calcined by increasing the air concentration from 15 to 30, 50, 70 and, finally, to 100 percent at 30 minute intervals and holding in 100 percent air for an additional 5 hours.

About 5 grams each of the calcined zeolites were then treated as follows:

0.1N HCl, 95°, 1 hour
1M NH$_4$Cl, 95°, 1 hour
2.0N HCl, 95°, 1 hour
1M NH$_4$Cl, 95°, 1 hour.

The results are summarized in Table 2 below.

TABLE 2

| | Dealuminization of Zeolite Beta | |
|---|---|---|
| Ex | Initial SiO$_2$/Al$_2$O$_3$ | Final SiO$_2$/Al$_2$O$_3$ |
| 6 | 21.3 | 280, 250* |
| 7 | 23 | 195 |
| 8 | 35 | 150 |

*Large sample (15 g.) used for this determination.

(2.5 g. zeolite per 200 ml water) and 1N HCl added slowly to obtain a 0.2N HCl concentration. The slurry was refluxed for 1 hour at 100° C. to form dealuminized HZSM-20 (USD) which was washed with water and dried at 120° C.

The product had a silica:alumina ratio of 226:1 by TGA/NH$_3$ desorption (20° C., min$^{-1}$, helium sweep), a crystallinity of 55 percent relative to an assumed value of 100 percent for the original NH$_4$ZSM-20 (crystallinity by X-ray peak determination) and an n-hexane cracking activity of 0.01 compared to 0.76 for the original NH$_4$ZSM-20 (100 mg sample at 400° C. at 100 torr in helium, sample calcined in air at 540° C. prior to use).

EXAMPLE 10

A sample of NaY zeolite having a silica:alumina ratio of 5.23:1 by bulk assay was converted to ultrastable zeolite Y by ammonium exchange and calcination in nitrogen as described above in Example 9, followed by ammoniation and ammonia exchange and deep bed calcination at 760° C. for 3 hours in a tightly packed and covered crucible. The ultrastable zeolite Y HY(US) so formed was again ammoniated and ammonium exchanged, followed by deep bed calcination at 815° C. for 3 hours.

Samples of the ultrastable zeolite Y were then extracted with HCl at 90° C. for 4 hours, using different acid concentrations. The extracted samples were then analyzed for structural silica:alumina ratio by bulk assay and TGA/NH$_3$ desorption. The n-hexane cracking activity was also determined using the same conditions as in Example 9. The results are set out in Table 3 below.

TABLE 3

| | | Dealuminization of Zeolite Y | | | |
|---|---|---|---|---|---|
| SAMPLE DESCRIPTION | PREPARATION | SiO$_2$/Al$_2$O$_3$ BULK ASSAY | SiO$_2$/Al$_2$O$_3$ TGA—NH$_3$ | CRACKING ACTIVITY N—HEXANE | ALPHA |
| NaY | | 5.23 | — | — | — |
| NH$_4$Y(US) | 760° C. 3 hrs | — | 3.47 | 0.54 | — |
| NH$_4$Y(US2D)0.2 | 815° C., 3 hrs covered 0.2 N HCl, 90° C. 4 hrs | 19.5 | 40.8–75.6$^{(1)}$ | 0.11 | — |
| NH$_4$Y(US2D)0.5 | 0.5 N HCl, 90° C. 4 hrs | 19.7 | 48.8 | 0.153 | 735 |
| NH$_4$Y(US2D2.0 | 2.0 N HCl, 90° C. 4 hrs | 279 | 1027 | 0.00015$^{(2)}$ | 0.4 |
| NH$_4$Y(US2D)0.2 | 0.2 N HCl, 90° C. hrs | 10 | 36–75.2$^{(1)}$ | 0.095 | — |

Notes:
$^1$Initial value prior to calcination at 500° C., pH decreases during titration above 600° C. in TGA.
$^2$Calculated from alpha and corrected to 750° F. at 30 kcal E$_a$.

EXAMPLE 9

Ammonium exchanged TEA NaZSM-20 (silica:alumina ratio 10:1) was calcined in flowing nitrogen at 300° C. for 4 hours, followed by heating to a final temperature of 500° C. over an additional 4 hours. The HNaZSM-20 so produced was ammoniated and then ammonium exchanged with 0.5M NH$_4$Cl under reflux at 100° C., washed free of chloride with water and dried at 120° C. The NH$_4$ZSM-20 was then calcined at 760° C. for 3 hours in a tightly packed and covered crucible to prevent ammonia and water from escaping readily. The ultrastable HZSM-20 (US) was ammoniated and ammonium exchanged with 1M NH$_4$Cl under reflux at 100° C. for 1 hour, washed with water and dried at 120° C. The dried NH$_4$ZSM-20 (US) was calcined at 815° C. for 3 hours in a tightly packed and covered crucible and after cooling the calcined product was slurried in water

EXAMPLE 11

Hydrocracking catalysts prepared from zeolites X, Y, ZSM-20 and beta were evaluated for hydrocracking using an Arab Light Heavy Gas Oil (HVGO) as feedstock at 400°–425° C., 7000 kPa, 0.4–2.0 LHSV, 1424 n.l.l.$^{-1}$ H$_2$/hydrocarbon.

The catalyst based on zeolite X was a commercial hydrocracking catalyst consisting of equal amounts of REX (silica:alumina ratio about 3:1) and amorphous silica-alumina (13 percent alumina) with about 4 percent nickel and 10 percent tungsten present as the hydrogenation component.

The Y, ZSM-20 and beta zeolites used had silica:alumina ratios of 5:1, 10:1 and 30:1, respectively. The hydrocracking catalysts were prepared using the magnesium exchanged zeolite (less than 0.5 percent sodium), pelleted with an equal amount of gamma alumina and impregnated to contain about 4 percent nickel and 10 percent tungsten.

In addition, highly siliceous zeolite Y and ZSM-20 were prepared by the methods described in Examples 9 and 10. The zeolite Y (Y (US2D)0.2) had a structural silica:alumina ratio of about 75:1 (TGA/NH$_3$ desorption) and the zeolite ZSM-20 a ratio of about 220:1. The high silica zeolite Y was used in the rare earth form and contained about 2 percent nickel and 7 percent tungsten. The high silica ZSM-20 was used in the magnesium form produced by exchange with 1N MgCl$_2$ solution at 90° C., followed by drying. The zeolites were mulled and pelleted with an equal weight (dry basis) of Kaiser (trade mark) alumina (hydrated Alpha-Al$_2$O$_3$) and calcined overnight at 500° C. The pellets were then sized to 30-40 mesh (Tyler; approximately 0.35-0.5 mm.) and impregnated with a solution of Ni(NO$_3$)$_2$ and ammonium metatungstate to obtain 4 percent nickel and 10 percent tungsten loadings. The catalysts were then calcined at 500° C. prior to loading the reactor. Before use, the catalysts were reduced and sulfided using 2 percent H$_2$S in hydrogen at 370° C., 1 Atm., 100 ml min$^{-1}$ flow rate for about 14 hours.

The results of the hydrocracking test are shown in the single FIGURE of the accompanying drawings which relates the distillate selectivity to the structural silica:alumina ratio at different conversions. The distillate selectivity is defined by reference to the amounts of the 165° C.-343° C. (330° F.-650° F.) fraction and the total 343° C.-fraction in the hydrocracker effluent as follows:

$$\text{Dist. select.} = \frac{165° \text{ C.-}343° \text{ C. fraction (wt)}}{\text{Total } 343° \text{ C.} - \text{fraction (wt)}} \times 100$$

The results in the FIGURE show that an increase in the silica:alumina ratio of the zeolite results in a corresponding increase in distillate selectivity over a wide range of conversions.

The catalysts referred to in the FIGURE were as follows:

X: A Ni-W/REX/SiO$_2$-Al$_2$O$_3$ catalyst based on REX (silica:alumina ratio of 12.5:1).
Y: A Ni-W/MgY/Al$_2$O$_3$ catalyst based on MgY (silica:alumina ratio of 5:1).
20: A Ni-W/MgZSM-20/Al$_2$O$_3$ catalyst based on MgZSM-20 (silica:alumina ratio of 10:1).
B: A Ni-W/Mg-beta/Al$_2$O$_3$ catalyst based on Mg-beta zeolite (silica:alumina ratio of 30:1).
SiY: A Ni-W/REY/Al$_2$O$_3$ catalyst based on the highly siliceous zeolite REY of Example 10 (silica:alumina ratio of 75:1).
Si20: A Ni-W/MgZSM-20/Al$_2$O$_3$ catalyst based on the highly siliceous MgZSM-20 of Example 9 (silica:alumina ratio of 220:1).

The three curves in the FIGURE relate the distillate selectivity to the structural silica:alumina ratio of the zeolite at conversions of 40, 60, and 80 percent and show that the selectivity increases with increasing structural silica:alumina ratio. cl EXAMPLES 12 AND 13

The effect of varying the structural silica:alumina ratio of the zeolite was demonstrated by hydrocracking an Arab Light HVGO over a ZSM-20 based hydrocracking catalyst. The zeolite was used in two forms, having structural silica:alumina ratios of 10:1 and 220:1 respectively. The catalyst was a Ni-W/MgZSM-20/Al$_2$O$_3$ hydrocracking catalyst (4% Ni, 10% W; 1:1 zeolite-:Al$_2$O$_3$). The feedstock composition, conditions used and product analysis are shown in Table 4 below, demonstrating that the use of higher silica:alumina ratios in the catalyst lead to a lower hydrogen consumption with a higher distillate yield and a decreased production of gas and napththa.

TABLE 4

| Hydrocracking over ZSM-20 Catalyst | | | |
|---|---|---|---|
| | Charge | Ex. 12 | Ex. 13 |
| Zeolite SiO$_2$/Al$_2$O$_3$ | — | 10:1 | 220:1 |
| Temp, °C. | — | 413 | 413 |
| Pressure, kPa | — | 7000 | 7000 |
| LHSV, 1 hr$^{-1}$ | — | 0.77 | 0.54 |
| H$_2$, n.l.l.$^{-1}$, Approx. | — | 1420 | 1420 |
| Conversion | — | 58.5 | 59.9 |
| H$_2$ Consumption | — | 1165 | 702 |
| Analysis: | | | |
| Gas + C$_4$ | — | 6.3 | 2.4 |
| C$_5$-165° C. | — | 23.8 | 14.2 |
| 165°-343° C. | — | 28.4 | 43.3 |
| 343° C. + | 100 | 41.5 | 40.1 |
| Pour Point, °C. | 40 | 21 | 24 |
| 95% TBP, °C. | 552 | 512 | 507 |

We claim:

1. A process for increasing the selectivity of the production of higher boiling distillate range product in hydrocracking reactions which can produce gasoline boiling range product and higher boiling distillate range product, which process comprises, contacting a feedstock to be hydrocracked in a hydrocracker, in the presence of hydrogen and under hydrocracking conditions, with a catalyst comprising a hydrogenation component and a zeolite which has a porous lattice structure having pores with a dimension greater than 6 Angstroms and a hydrocarbon sorption capacity for hexane of at least 6 percent and has a framework silica:alumina ratio of at least about 50:1, whereby the selectivity of the process for production of the higher boiling distillate range product is preferentially increased, wherein the distillate selectivity is defined by reference to the amounts of the 165° C.-343° C. (330° F.-650° F.) fraction and the total 343° C.-fraction in the hydrocracker effluent as follows:

$$\text{Dist. Select.} = \frac{165° \text{ C.} - 343° \text{ C. fraction (wt)} \times 100}{\text{Total } 343° \text{ C.} - \text{fraction (wt)}}.$$

2. A process according to claim 1 in which the zeolite is zeolite Y.

3. A process according to claim 1 in which the zeolite is zeolite ZSM-20.

4. A process according to claim 1 in which the zeolite has a Constraint Index of 0.5 to 2.0.

5. A process according to claim 1 in which the zeolite has a silica:alumina ratio of at least 100:1.

6. A process according to claim 5 in which the zeolite has a silica:alumina ratio of at least 200:1.

7. A process according to claim 1 in which the hydrogenation component comprises a noble metal of Group VIIIA of the Periodic Table.

8. A process according to claim 1 in which the hydrogenation component comprises a metal of Groups VA, VIA or VIIIA of the Periodic Table.

9. A process according to claim 1 in which the hydrogenation component comprises nickel, cobalt, molybdenum, tungsten or a combination of these metals.

10. A process according to claim 1 in which the feedstock is contacted with the catalyst in the presence of hydrogen at a temperature of 230° C. to 500° C., a pressure of 500 to 20,000 kPa and a LHSV of 0.1 to 20.

11. A process according to claim 1 in which the zeolite is an ultrastable zeolite Y which has been acid extracted with a 0.5 normal HCl for four hours at 90° C. and has a silica:alumina ratio by bulk assay of about 20:1 and a structural silica:alumina ratio of about 50:1.

12. A process according to claim 1 wherein said zeolite is ZSM-20 which has been subjected to acid extraction to produce a zeolite with a structural silica:alumina ratio of at least about 220:1.

13. A process according to claim 1 which comprises contacting a hydrocarbon feedstock in the presence of hydrogen and under hydrocracking conditions with a catalyst comprising a hydrogenation component and, as an acidic component, zeolite ZSM-20 having a silica:alumina ratio of at least 50:1.

14. A process according to claim 13 in which the zeolite has a silica/alumina ratio of at least 100:1.

15. A process according to claim 13 in which the zeolite has silica:alumina ratio of at least 200:1.

16. A process according to claim 13 in which the hydrogenation component comprises a noble metal of Group VIIIA of the periodic Table.

17. A process according to claim 13 in which the hydrogenation component comprises a metal of Groups VA, VIA or VIIIA of the Periodic Table.

18. A process according to claim 13 in which the hydrogenation component comprises nickel, cobalt, molybdenum, tungsten of a combination of these metals.

19. A process according to claim 13 in which the feedstock is contacted with the catalyst in the presence of hydrogen at a temperature of 230° C. to 500° C., a pressure of 500 to 20,000 kPa and an LHSV of 0.1 to 20.

20. A process according to claim 13 wherein said ZSM-20 has been subjected to acid extraction to produce a zeolite with a structural silica: alumina ratio of at least about 220:1.

21. A process according to claim 2, wherein the feedstock is contacted with the catalyst in the presence of hydrogen at a temperature of 230° C. TO 500° C., a pressure of 500 to 20,000 kPa and a LHSV of 0.1 to 20.

22. A process according to claim 11, in which the feedstock is contacted with said catalyst in the presence of hydrogen at a temperature of 230° C. to 500° C., a pressure of 500 to 20,000 kPa and a LHSV of 0.1 to 20.

* * * * *